United States Patent [19]

Press

[11] Patent Number: 4,703,120
[45] Date of Patent: Oct. 27, 1987

[54] FURO(3,4-D)PYRIMIDINE-2,4-DIONE DERIVATIVES AND INTERMEDIATES THEREOF

[75] Inventor: Jeffery B. Press, Rocky Hill, N.J.

[73] Assignee: Ortho Pharmaceutical Corporation, Raritan, N.J.

[21] Appl. No.: 856,561

[22] Filed: Apr. 28, 1986

[51] Int. Cl.[4] .............. C07D 491/048; C07D 405/02; C07D 498/04
[52] U.S. Cl. .................................. 544/278; 544/379; 544/91
[58] Field of Search ........................................ 544/278

[56] References Cited

U.S. PATENT DOCUMENTS 4,001,412  1/1977  Hirahashi et al. ............... 544/278

FOREIGN PATENT DOCUMENTS 471485  2/1951  Canada ............................. 544/278
0150469  7/1985  European Pat. Off. .
057612  2/1967  United Kingdom .

Primary Examiner—Donald G. Daus
Assistant Examiner—Barbara Cassatt
Attorney, Agent, or Firm—Benjamin F. Lambert

[57] ABSTRACT

The synthesis of furo[3,4-d]pyrimidine-2,4-dione derivatives and their urea intermediates is described. The novel urea intermediates and furo[3,4-d]pyrimidine-2,4-dione derivatives are general vasodilating agents and anti-hypertensive agents. The compounds are useful as cardiovascular agents.

6 Claims, No Drawings

FURO(3,4-D)PYRIMIDINE-2,4-DIONE DERIVATIVES AND INTERMEDIATES THEREOF

BACKGROUND OF THE INVENTION

1. Field of the Invention

The present invention relates to novel furo[3,4-d]pyrimidine-2,4-dione derivatives of general formula I:

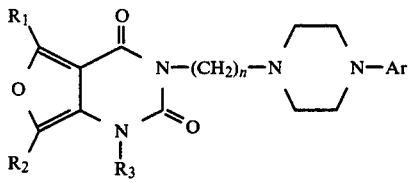

or their intermediates of general formula II:

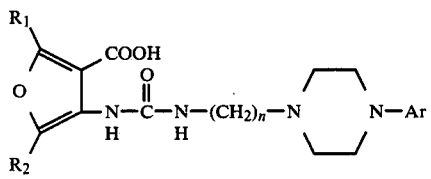

as described further below. The derivatives and intermediates are useful as cardiovascular agents, such as antihypertensive or general vasodilating agents.

2. Description of the Prior Art

No examples of furopyrimidine compounds have been seen in the prior art. However, several thienopyrimidine compounds have been previously described which have a variety of biological activity. For example, *Chem. Abstr.* 87, 201452 describes thienopyrimidine-2,4-dione compounds of the formula

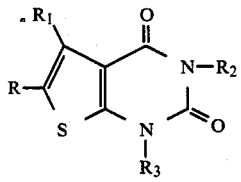

in which $R_2$ is methyl or phenyl and $R_3$ is acetylenic chains with amine termini. No utility was disclosed for these compounds.

Belgian Patent No. 799238A describes thienopyrimidine-2-one compounds as CNS, uricosuric, antiviral or antiinflammatory agents. The compounds have the general formula

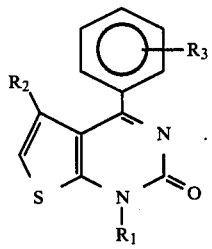

Belgian Patent No. 796003 describes similar compounds having an additional substituent on the thiophene ring. The latter compounds have the same activity as the former compounds.

British Patent No. 1,057612 describes several thienopyrimidine compounds having different activities such as fungistatic, bacteriostatic, cytostatic, antiphlogistic, CNS stimulating and cardiovascular activity. Compounds of the formula

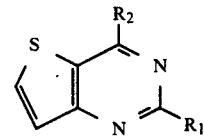

where $R_1$ or $R_2$ are N-methylpiperazine are said to have good cardiovascular effects. Additional compounds include those of the following general formulas:

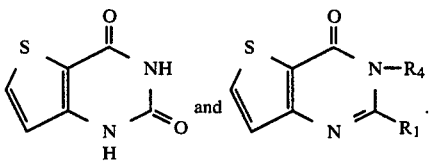

Derwent Accession Number 66-23,767/00 describes compounds of the formula

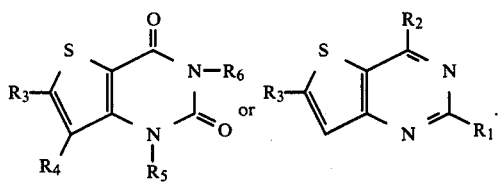

which have coronary or peripheral vasodilator activity as well as CNS activity. In the dione compounds, $R_5$ and $R_6$ may be alkyl or aryl.

*Chem. Abs.* 104, 19606q (EP 150469) describes thienopyrimidine compounds which are antidepressants and which have the formula:

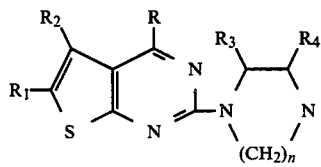

where R may be aryl or thieno and $R_1$ and $R_2$ may be hydrogen, alkyl, halo or alkylene.

Finally, H. K. Gaklar et al., *Indian J. Chem. Sec. B*, 24B, 432 (1985) describes the preparation of thienopyrimidine-4-ones having the formula:

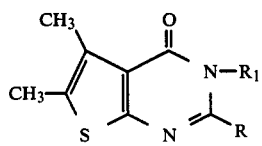

No biological activity was disclosed for these compounds.

None of the thienopyrimidine compounds of the prior art discussed above contain an N-alkyl-N-arylpiperazine moiety, i.e.,

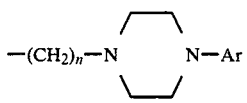

at the 3-position. Furthermore, several of the compounds are not diones and do not contain the same substituents at the 1-position of the present invention.

SUMMARY OF THE INVENTION

The present invention is directed to furo[3,4-d]pyrimidine compounds of the formula

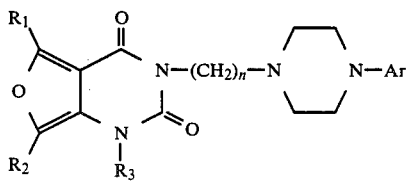

where
- $R_1$ and $R_2$ may be the same or different and may be hydrogen or $C_1$-$C_3$ alkyl;
- $R_3$ may be hydrogen, $C_1$-$C_{10}$ alkyl, $C_3$-$C_8$ branched-chain alkyl, $C_3$-$C_8$ alkenyl, $C_3$-$C_6$ alkynyl, —$(CH_2)_m$—$CO_2R_4$ or —$COR_5$;
- $R_4$ may be hydrogen, $C_1$-$C_3$ alkyl, pharmaceutically acceptable alkali metal ion, pharmaceutically acceptable alkaline earth metal ion or a pharmaceutically acceptable quaternary ammonium species;
- $R_5$ may be $C_1$-$C_{10}$ alkyl, $C_3$-$C_{10}$ branched-chain alkyl, $C_1$-$C_3$ alkoxy, or Ar;
- Ar may be

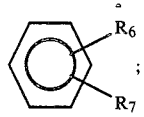

- $R_6$ and $R_7$ may be the same or different and may be hydrogen, F, Cl, Br, $NO_2$, $CF_3$, $C_1$-$C_3$ alkyl, acetyl, $C_1$-$C_3$ alkoxy or acetamido;
- m may be 2–6; and
- n may be 2–6.

The present invention is further directed to intermediates of the compounds of formula I having the formula

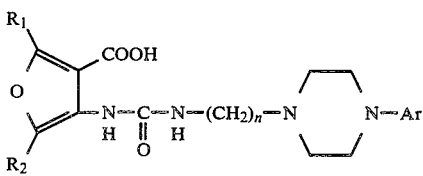

where
$R_1$, $R_2$, Ar and n are as defined above.

The compounds of formula I or II are useful as cardiovascular agents, such as antihypertensive agents or general vasodilating agents, especially renal vasodilating agents.

DETAILED DESCRIPTION OF THE INVENTION

The invention in its broadest aspects relates to furo[3,4-d]pyrimidine-2,4-dione compounds and intermediates thereof which have cardiovascular activity, such as antihypertensive activity or general vasodilatory activity, in mammals. The furo[3,4-d]pyrimidine-2,4-dione compounds of the invention demonstrating a cardiovascular activity are shown by formula I above. The intermediates of these compounds which also have a cardiovascular activity are shown by formula II above. The furo[3,4-d]pyrimidine-2,4-dione compounds and intermediates which have a cardiovascular activity all contain a nitrogen, either in the pyrimidine ring of the furo[3,4-d]pyrimidine-2,4-diones or in the urea moiety of the intermediates, which is substituted by the group

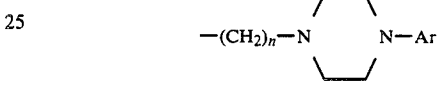

where n and Ar are as defined above.

The preferred compounds of the present invention are those wherein $R_1$ is hydrogen or alkyl; $R_2$ is hydrogen or alkyl; $R_3$ is hydrogen, alkyl, —$(CH_2)_m$—$CO_2R_4$ or —$COR_5$; $R_4$ is alkyl; $R_5$ is alkyl, branched-chain alkyl, alkoxy or phenyl; Ar is phenyl, methylphenyl, chlorophenyl, fluorophenyl or methoxyphenyl; m is 2–4; and n is 2.

The compounds of formulas I and II can be prepared as shown in the following scheme.

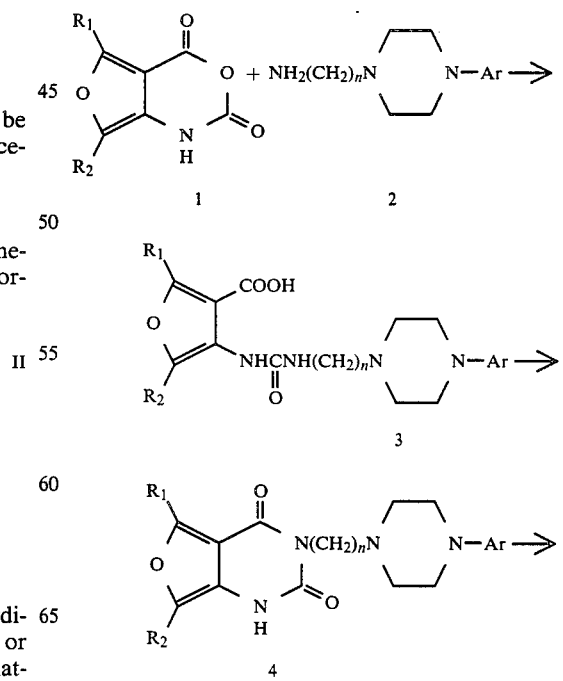

-continued

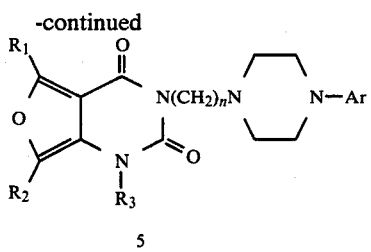

5

The compounds of formula II are prepared as follows:

The anhydride 1 is suspended in an inert solvent and reacted with the amine 2 at about 0° C. to about 100° C. for about 1 hour to about 7 days to produce the urea 3 as an off-white solid. The anhydride 1 is prepred by the procedure of J. B. Press, et al., *J. Org. Chem.* 46, 3853 (1981) when $R_1=R_2=H$. When $R_1=R_2=CH_3$, the anhydride 1 is prepared by a similar reaction sequence using 3,4-dicarboethoxy-2,5-dimethylfuran, prepared as described by M. S. Newman, et al., *J. Org. Chem.* 20, 3482 (1973). The aminoalkylpiperazine 2 is prepared by the method of R. P. Mull, et al., *J. Med. Chem.* 46, 944 (1962), S. Hayao, et al., *J. Org. Chem.* 26, 3415 (1961) or Y. H. Wu, et al., *J. Med. Chem.* 12, 876 (1969). New piperazine derivatives are prepared by using analogous procedures. Inert solvents which may be utilized include ether, dioxane, glyme, diglyme and tetrahydrofuran.

The compounds of formula I are prepared as follows:

The urea 3 is reacted with a dehydrating agent in an inert solvent at about 25° C. to about 100° C. for about 1 to about 24 hours to produce the furan[3,4-d]pyrimidine-2,4-dione 4 as a solid. Suitable dehydrating agents include thionyl chloride, phosphorous pentoxide, carbonyldiimidazole or dicyclohexyl-carbodiimide. Appropriate inert solvents can include methylene chloride, chloroform, benzene, toluene, ether, tetrahydrofuran or dioxane.

The dione 4 can be alkylated at the 1-position to produce the alkylated derivatives 5 by treatment in an inert solvent with a strong base and subsequent treatment with an alkyl halide. Suitable inert solvents include tetrahydrofuran, glyme, dioxane, dimethylformamide or dimethyl sulfoxide. The preferred strong bases are sodium hydride or lithium diisopropylamide. Alkyl halides include methyl bromide, butyl bromide, allyl bromide, methyl 4-bromobutyrate, propargyl iodide and the like.

The carboxylic acid derivative of 5, i.e., $R_3$ is $-(CH_2)_mCO_2H$, can be prepared by dissolving the carboxylic ester derivative of 5, i.e., $R_3$ is $-(CH_2)_mCO_2R_4$ where $R_4$ is a lower alkyl (prepared as in the preceding paragraph), in an aqueous alcoholic solvent and treating with an alkali metal base at about 25° C. for about 3 to about 24 hours. Suitable alcohols include methanol and ethanol. Preferred bases are sodium hydroxide and potassium hydroxide.

The carboxylic acids may be converted to their corresponding pharmaceutically acceptable salts by dissolving the acids in an alcoholic solvent, for example methanol or ethanol, and treating them with an appropriate base. Appropriate bases include sodium hydroxide, potassium hydroxide, calcium hydroxide, triethylamine, tetrabutylammonium hydroxide and the like. The salts are obtained as solids after removal of the solvent.

The acylated derivatives 5 can be produced by refluxing the dione 4 with acylating agents such as acetic anhydride for about 1 to about 24 hours. Alternatively, the acylated derivatives can be prepared by treating the dione 4 with a strong base and an acid chloride in a polar solvent. The preferred strong bases are sodium hydride and lithium diisopropylamide. Suitable polar solvents include dimethyl sulfoxide, dimethylformamide and N-methylpyrrolidone. Acid chlorides include acetyl chloride, trimethylacetyl chloride, benzoyl chloride and the like. A final approach is to treat the dione 4 with an amine base such as triethylamine and an acid chloride.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other intredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 0.5 to about 100 mg/kg, and preferably from about 1 to about 5 mg/kg of the active ingredient.

The following examples describe the invention in greater particularity and are intended to be a way of illustrating but not limiting the invention.

EXAMPLE 1

1-(3-Carboxyfuran-4-yl)-3-[4-(2-methoxyphenyl)piperazin-1-yl]ethylurea

1-[1-(2-Aminoethyl)]-4-(2-methoxyphenyl)piperazine (R. P. Mull, et al., *J. Med. Chem.* 5, 944 (1962)) (9.9 g, 42.1 mmol) was added to a suspension of 4H-furo[3,4-d][1,3]oxazine-2(1H), 4-dione (J. B. Press, et al., *J. Org. Chem.* 46, 3853 (1981)) (6.25 g, 40.8 mmol) in tetrahydrofuran (100 ml). The mixture was stirred at room temperature for 2.5 days. The solvent was removed in vacuo and the residue was triturated in hot water. The resultant solid was collected by filtration and washed with water to give the product (14.3 g, 90% yield) as an off-white solid, mp 220°–222° C. (dec). IR (KBr) 1640, 1690, 2320–3700 and 3280 cm$^{-1}$; mass spectrum m/z 389 (MH+); $^1$H NMR (TFA) δ 3.57–4.57 (m, 12H, NC$\underline{H}_2$), 4.07 (s, 3H, Ph-OC$\underline{H}_3$), 7.03–8.27 (m, 6H, Ph-$\underline{H}$, furan-$\underline{H}$).

3-[2-[4-(2-Methoxyphenyl)piperazin-1-yl]ethyl]-furo[3,4-d]pyrimidine-2,4-dione A mixture of 1-(3-carboxyfuran-4-yl)-3-[4-(2-methoxyphenyl)piperazin-1-yl]ethylurea (4.0 g, 10.3 mmol) and 1,1'-carbonyldiimidazole (2.2 g, 13.4 mmol) in tetrahydrofuran (100 ml) was heated to reflux for 1.5 hours. The solvent was removed in vacuo, and the residue was triturated in hot water. The resultant brown solid was collected by filtration, washed with water and triturated in hot ethanol to give the product (1.8 g, 47% yield) as an off-white solid, mp 194°–196° C. (dec). IR (KBr) 2820, 1715 and 1675 cm$^{-1}$; mass spectrum m/z 371 (MH+); $^1$H NMR (Me$_2$SO-d$_6$) δ 2.38–2.75 (m, 6H, NCH$_2$), 2.80–3.10 (m, 4H, NCH$_2$), 3.77 (s, 3H, Ph-OCH$_3$), 3.98 (t, J=7 Hz, 2H, 3-CH$_2$), 6.77–7.00 (m, 4H, Ph-H), 7.63 (d, J=2 Hz, 1H, furan-H), 8.43 (d, J=2 Hz, 1H, furan-H) and 10.82 (brs, 1H, NH).

Theor. C$_{19}$H$_{22}$N$_4$O$_4$: C, 61.61; H, 5.99; N, 15.13. Found: C, 61.16; H, 6.04; N, 14.98.

EXAMPLE 2

1-(3-Carboxyfuran-4-yl)-3-[4-(2-methylphenyl)piperazin-1-yl]ethylurea

1-[1-(2-Aminoethyl)]-4-(2-methylphenyl)piperazine (R. P. Mull, et al., *J. Med. Chem.* 5, 944 (1962)) (4.73 g, 21.6 mmol) in tetrahydrofuran (20 ml) was added to a suspension of 4H-furo[3,4-d][1,3]oxazine-2(1H), 4-dione (J. B. Press, et al., *J. Org. Chem.* 46, 3853 (1981)) (3.0 g, 19.6 mmol) in tetrahydrofuran (100 ml). The mixture was stirred at room temperature for 16 hours. The solvent was removed in vacuo and the residue was triturated in hot water. The resultant solid was collected by filtration and washed with water to give the product (7.2 g, 90% yield) as an off-white solid, mp 212°–216° C. (dec). IR (KBr) 1625, 1690, 2000–2420 and 3300 cm$^{-1}$; mass spectrum m/z 373 (MH+); $^1$H NMR (TFA) δ 2.63 (s, 3H, Ph-CH$_3$), 3.60–4.70 (m, 12H, NCH$_2$), 7.37–7.68 (m, 4H, Ph-H), 7.80 (brs, 1H, furan-H), 8.15 (brs, 1H, furan-H).

Theor. C$_{19}$H$_{24}$N$_4$O$_4$: C, 61.27; H, 6.50; N, 15.04. Found: C, 61.51; H, 6.65; N, 14.76.

3-[2-[4-(2-Methylphenyl)piperazin-1-yl]ethyl]furo[3,4-d]pyrimidine-2,4-dione A mixture of 1-(3-carboxyfuran-4-yl)-3-[4-(2-methylphenyl)piperazin-1-yl]ethylurea (5.0 g, 13.4 mmol) and 1,1'-carbonyldiimidazole (3.04 g, 18.8 mmol) in tetrahydrofuran (100 ml) was heated to reflux for 1.5 hours. The solvent was removed in vacuo and the residue was triturated in hot water. The resultant brown solid was collected by filtration, washed with water and triturated in hot ethanol to give the product (2.31 g, 48% yield) as an off-white solid, mp 195°–196° C. (dec). IR (KBr) 1665, 1700, 2820 and 3125 cm$^{-1}$; mass spectrum m/z 355 (MH+); $^1$H NMR (Me$_2$SO-d$_6$) δ 2.23 (s, 3H, Ph-CH$_3$), 2.37–2.93 (m, 10H, NCH$_2$), 3.98 (t, J=7 Hz, 2H, 3-CH$_2$), 6.70–7.30 (m, 4H, Ph-H), 7.60 (d, J=2 Hz, 1H, furan-H), 8.42 (d, J=2 Hz, 1H, furan-H) and 10.87 (brs, 1H, NH).

Theor. C$_{19}$H$_{22}$N$_4$O$_3$: C, 64.39; H, 6.26; N, 15.81. Found: C, 64.62; H, 6.13; N, 15.87.

EXAMPLE 3

1-(3-Carboxyfuran-4-yl)-3-(4-phenylpiperazin-1-yl)ethylurea

1-[1-(2-Aminoethyl)]-4-phenylpiperazine (S. Hayao and R. N. Schut, *J. Org. Chem.* 26, 3415 (1961)) (4.42 g, 21.6 mmol) was added to a suspension of 4H-furo[3,4-d][1,3]oxazine-2(1H), 4-dione (J. B. Press, et al., *J. Org. Chem.* 46, 3853 (1981)) (3.0 g, 19.6 mmol) in tetrahydrofuran (50 ml). The mixture was stirred at room temperature for 16 hours. The solvent was removed in vacuo, and the residue was triturated in hot water. The resultant solid was collected by filtration and washed with water to give the product (6.0 g, 77% yield) as an off-white solid, mp 219°–221° C. (dec). IR (KBr) 1555, 1620, 1670, 1930–2600, 2800–3640 and 3260 cm$^{-1}$; mass spectrum m/z 359 (MH+); $^1$H NMR (TFA) δ 3.65–4.67 (m, 12H, NCH$_2$), 7.37–8.27 (m, 6H, Ph-H, furan-H).

3-[2-(4-Phenylpiperazin-1-yl)ethyl]furo[3,4-d]pyrimidine-2,4-dione

A mixture of 1-(3-carboxyfuran-4-yl)-3-(4-phenylpiperazin-1-yl)ethylurea (5.0 g, 14.0 mmol) and 1,1'-carbonyldiimidazole (3.16 g, 19.4 mmol) in tetrahydrofuran (100 ml) was refluxed for 1.5 hours. The solvent was removed in vacuo, and the residue was triturated in hot water. The resultant brown solid was collected by filtration, washed with water and purified by flash chromatography on silica gel 60 (250 g) using 2% methanol in methylene chloride as eluant to give the product (3.05 g, 64% yield) as a colorless solid, mp 209°–210° C. (dec). IR (KBr) 1660, and 1725 cm$^{-1}$; mass spectrum m/z 341 (MH+); $^1$H NMR (Me$_2$SO-d$_6$) δ 2.32–2.80 (m, 6H, NCH$_2$), 2.88–3.28 (m, 4H, NCH$_2$), 3.98 (t, J=7 Hz, 2H, 3-CH$_2$), 6.60–7.38 (m, 5H, Ph-H), 7.60 (d, J=2 Hz, 1H, furan-H), 8.43 (d, J=2 Hz, 1H, furan-H) and 10.87 (brs, 1H, NH).

Theor. C$_{18}$H$_{20}$N$_4$O$_3$: C, 63.52; H, 5.92; N, 16.46. Found: C, 63.44; H, 5.77; N, 16.32.

EXAMPLE 4

1-(3-Carboxyfuran-4-yl)-3-[4-(2-chlorophenyl)piperazin-1-yl]ethylurea

4H-Furo[3,4-d][1,3]oxazine-2(1H),4-dione (J. B. Press, et al., *J. Org. Chem.* 46, 3853 (1981)) (1.97 g, 12.9 mmol) was added to a solution of 1-[1-(2-aminoethyl)]-4-(2-chlorophenyl)piperazine (R. P. Mull, et al., *J. Med. Chem.* 5, 944 (1962)) (3.4 g, 14.2 mmol) in tetrahydrofuran (300 ml), and the resultant mixture was stirred at room temperature for 16 hours. The white solid precipitate was collected by filtration, washed with tetrahydrofuran and air-dried to give the product (4.8 g, 95% yield) as a colorless solid, mp 219°–220° C. IR (KBr) 1574, 1628, 1682, and 1900–2700 cm$^{-1}$; mass spectrum m/z 393 (MH+); $^1$H NMR (TFA) δ3.52–4.67 (m, 12H, NCH$_2$), 7.48–8.00 (m, 5H, Ph-H, furan-H), 8.18 (brs, 1H, furan-H).

3-[2-[4-(2-Chlorophenyl)piperazin-1-yl]ethyl]furo[3,4-d]pyrimidine-2,4-dione A mixture of 1-(3-carboxyfuran-4-yl)-3-[4-(2-chlorophenyl)piperazin-1-yl]ethylurea (4.6 g, 11.7 mmol) and 1,1'-carbonyldiimidazole (2.37 g, 14.6 mmol) in tetrahydrofuran (80 ml) was heated to reflux for 2 hours. The solvent was removed in vacuo and the residue was triturated in hot water. The resultant solid was collected by filtration, washed with water and triturated in hot ethanol to give the product (3.19 g, 73% yield) as a colorless solid, mp 215°–217° C. (dec). IR (KBr) 1649, 1653, 1673, 1706, 3129 and 3142 cm$^{-1}$; mass spectrum m/z 375 (MH+); $^1$H NMR (Me$_2$SO-d$_6$) δ 2.40–2.76 (m, 6H, NCH$_2$), 2.82–3.17 (m, 4H, NCH$_2$), 3.98 (t, J=7 Hz, 2H, 3-CH$_2$), 6.80-7.50 (m, 4H, Ph-H), 7.60 (d, J=2 Hz, 1H, furan-H), 8.42 (d, J=2 Hz, 1H, furan-H) and 10.88 (brs, 1H, NH).

Theor. C$_{18}$H$_{19}$ClN$_4$O$_3$: C, 57.68; H, 5.11; N, 14.95. Found: C, 57.48; H, 5.10; N, 15.30.

EXAMPLE 5

3-[2-[4-(3-Methoxyphenyl)piperazin-1-yl]ethyl]-furo[3,4-d]pyrimidine-2,4-dione

1-[1-(2-Aminoethyl)]-4-(3-methoxyphenyl)piperazine (R. P. Mull, et al., *J. Med. Chem.* 5, 944 (1962)) (5.07 g, 21.6 mmol) was added to a suspension of 4H-furo[3,4-d][1,3]oxazine-2(1H), 4-dione (J. B. Press, et al., *J. Org. Chem.* 46, 3853 (1981)) (6.25 g, 40.8 mmol) in tetrahydrofuran (100 ml). The mixture was stirred at room temperature for 16 hours. 1,1'-Carbonyldiimidazole (7.0 g, 43.2 mmol) was added to the mixture, and the mixture was heated to reflux for 1.5 hours. The solvent was removed in vacuo and the residue was triturated in hot water. The resultant brown solid was collected by filtration, washed with water and purified by flash chromatography on silica gel 60 (250 g) eluted with 2% methanol in methylene chloride to give the product (4.70 g, 64% yield) as a colorless solid, mp 174°-175° C. (dec). IR (KBr) 1665 and 2000-3220 cm$^{-1}$; mass spectrum m/z 371 (MH+); $^1$H NMR (Me$_2$SO-d$_6$) δ 2.33-2.77 (m, 6H, NCH$_2$), 2.87-3.37 (m, 4H, NCH$_2$), 3.70 (s, 3H, Ph-OCH$_3$), 3.98 (t, J=7 Hz, 2H, 3-CH$_2$), 6.17-6.60 (m, 3H, Ph-H), 6.83-7.25 (m, 1H, Ph-H), 7.58 (d, J=2 Hz, 1H, furan-H), 8.42 (d, J=2 Hz, 1H, furan-H) and 10.83 (brs, 1H, NH).

Theor. C$_{19}$H$_{22}$N$_4$O$_4$.¼H$_2$O: C, 60.87; H, 6.05; N, 14.94. Found: C, 60.80; H, 6.16; N, 14.87.

EXAMPLE 6

3-[2-[4-(4-Methoxyphenyl)piperazin-1-yl]ethyl]-furo[3,4-d]pyrimidine-2,4-dione

4H-Furo[3,4-d][1,3]oxazine-2(1H), 4-dione (J. B. Press, et al., *J. Org. Chem.* 46, 3853 (1981)) (1.95 g, 12.7 mmol) was added to a solution of 1-[1-(2-aminoethyl)]-4-(4-methoxyphenyl)piperazine (Y. H. Wu, et al., *J. Med. Chem.* 12, 876 (1969)) (3.31 g, 14.1 mmol) in tetrahydrofuran (250 ml). The mixture was stirred at room temperature for 16 hours. 1,1'-Carbonyldiimidazole (3.1 g, 19.1 mmol) was added to the mixture, and the mixture was heated to reflux for 1.5 hours. The solvent was removed in vacuo and the residue was triturated in hot water. The resultant brown solid was collected by filtration, washed with water and purified by flash chromatography on silica gel 60 (350 g) using 2% methanol in methylene chloride as eluant to give the product (2.76 g, 59% yield) as a coloress solid, mp 215°-216° C. (dec). IR (KBr) 1648, 1662 and 1732 cm$^{-1}$; mass spectrum m/z 371 (MH+); $^1$H NMR (Me$_2$SO-d$_6$) δ 2.33-2.72 (m, 6H, NCH$_2$), 2.78-3.13 (m, 4H, NCH$_2$), 3.65 (s, 3H, Ph-OCH$_3$), 3.97 (t, J=7 Hz, 2H, 3-CH$_2$), 6.68-6.88 (m, 4H, Ph-H), 7.57 (d, J=2 Hz, 1H, furan-H), 8.38 (d, J=2 Hz, 1H, furan-H) and 10.82 (brs, 1H, NH).

Theor. C$_{19}$H$_{22}$N$_4$O$_4$: C, 61.61; H, 5.99; N, 15.13. Found: C, 62.03; H, 6.00; N, 15.50.

EXAMPLE 7

2,5-Dimethyl-3,4-furandicarboxylic Acid Monoethyl Ester

A solution of sodium hydroxide (1.86 g, 46.3 mmol) in water (30 ml) was added to a solution of 3,4-dicarbethoxy-2,5-dimethylfuran (M. S. Newman and J. A. Cella, *J. Org. Chem.* 20, 3482 (1973)) in ethanol (250 ml) at 5° C. The mixture was stirred at room temperature for 2.5 days. The solvent was removed in vacuo, and the residue was dissolved in water (100 ml) and washed with methylene chloride (2×100 ml). The aqueous solution was acidified with 1N hydrochloric acid. The white precipitate was collected by filtration, washed with water and air-dried to give the product (5.03 g, 51% yield) as a colorless solid, mp 79°-81° C. IR (KBr) 1592, 1631 and 1725 cm$^{-1}$; mass spectrum m/z 213 (MH+); $^1$H NMR (CDCl$_3$) δ 1.43 (t, J=7 Hz, 3H, CH$_2$CH$_3$), 2.58 (s, 3H, CH$_3$), 2.65 (s, 3H, CH$_3$), 4.43 (q, J=7 Hz, 2H, CH$_2$CH$_3$).

Theor. C$_{10}$H$_{12}$O$_5$: C, 56.60; H, 5.70. Found: C, 56.17; H, 5.62.

2,5-Dimethyl-3,4-furandicarboxylic Acid Monohydrazide

Hydrazine (3.5 ml, 0.11 mol) was added to a solution of 2,5-dimethyl-3,4-furandicarboxylic acid monoethyl ester (5.0 g, 24 mmol) in ethanol (200 ml), and the mixture was heated to reflux for 16 hours. The solution was cooled to 5° C., and the resultant precipitate was collected by filtration and washed with ethanol. The solid was dissolved in water (100 ml), and the solution was acidified to pH 3 with 1N HCl. The resultant white solid precipitate was collected by filtration and washed with water to give the product (3.4 g, 73% yield) as a colorless solid, mp>300° C. IR (KBr) 1579, 1633 and 1659 cm$^{-1}$; mass spectrum m/z 199 (MH+); $^1$H NMR (TFA) δ 2.71 (s, 3H, CH$_3$), 2.75 (s, 3H, CH$_3$).

Theor. C$_8$H$_{10}$O$_4$N$_2$: C, 48.48; H, 5.09; N, 14.14. Found: C, 48.28; H, 5.48; N, 13.77.

2,5-Dimethyl-4H-furo[3,4-d][1,3]oxazine-2(1H),4-dione

Sodium nitrite (1.3 g, 18.3 mmol) in water (10 ml) was added with rapid stirring to a suspension of 2,5-dimethyl-3,4-furandicarboxylic acid monohydrazide (3.3 g, 16.6 mmol) in ethanol free chloroform (80 ml) and 3N HCl (20 ml) at 5° C. The mixture was stirred at room temperature for 1 hour, and the organic phase was separated and dried over MgSO$_4$. The chloroform solution was heated to reflux for 16 hours, and concentrated in vacuo to a volume of 50 ml. Upon cooling to 0° C., a solid crystallized from solution and was collected by filtration, washed with chloroform and air-dried to give the product (1.72 g, 57% yield) as an off-white solid, mp 191°-193° C. IR (KBr) 1600, 1694, 1727 and 1792 cm$^{-1}$; mass spectrum m/z 182 (MH+); $^1$H NMR (Me$_2$SO-d$_6$) δ 2.28 (s, 3H, CH$_3$), 2.52 (s, 3H, CH$_3$), 11.15 (brs, 1H, NH).

Theor. C$_8$H$_7$O$_4$N: C, 53.04; H, 3.90; N, 7.73. Found: C, 52.86; H, 3.84; N, 7.62.

2,5-Dimethyl-1-(3-carboxyfuran-4-yl)-3-[4-(2-methoxyphenyl)piperazin-1-yl]ethylurea 1-[1-(2-Aminoethyl)]-4-(2-methoxyphenyl)piperazine (R. P. Mull, et al., *J. Med. Chem.* 5, 944 (1962)) (2.8 g, 11.8 mmol) was added to a solution of 2,5-dimethyl-4H-furo[3,4-d][1,3]oxazine-2(1H),4-dione (1.65 g, 9.11 mmol) in tetrahydrofuran (80 ml). The mixture was stirred at room temperature for 16 hours. The resultant precipitate was collected by filtration, washed with tetrahydrofuran and air-dried to give the product (3.5 g, 92% yield) as a colorless solid, mp 193°-196° C. IR (KBr) 1686 and 1670 cm$^{-1}$; mass spectrum m/z 417 (MH+); $^1$H NMR (Me$_2$SO-d$_6$) δ 2.13 (s, 3H, CH$_3$), 2.30–3.42 (s, 12H, NCH$_2$), 2.44 (s, 3H, Ph-OCH$_3$), 6.61–7.22 (m, 4H, Ph-H).

5,7-Dimethyl-3-[2-[4-(2-methoxyphenyl)piperazin-1-yl]ethyl]furo[3,4-d]pyrimidine-2,4-dione A mixture of 2,5-dimethyl-1-(3-carboxyfuran-4-yl)-3-[4-(2-methoxyphenyl)piperazin-1-yl]ethylurea (3.32 g, 7.97 mmol) and 1,1′-carbonyldiimidazole (1.68 g, 10.4 mmol) in tetrahydrofuran (100 ml) was heated to reflux for 1.5 hours. The solvent was removed in vacuo, and the residue was triturated in hot water. The resultant brown solid was collected by filtration, washed with water and triturated in hot ethanol to give the product (2.65 g, 83% yield) as a colorless solid, mp 224°–225° C. (dec). IR (KBr) 2823, 1717, 1695 and 1667 cm$^{-1}$; mass spectrum m/z 399 (MH$^+$); $^1$H NMR (Me$_2$SO-d$_6$) δ 2.09–3.31 (m, 10H, NCH$_2$), 2.34 (s, 3H, CH$_3$), 2.59 (s, 3H, CH$_3$), 3.87 (s, 3H, Ph-OCH$_3$), 4.14 (t, J=7Hz, 2H, 3-CH$_2$), 6.76–7.16 (m, 4H, Ph-H), and 10.82 (brs, 1H, NH).

Theor. C$_{21}$H$_{26}$N$_4$O$_4$: C, 63.30; H, 6.58; N, 14.06. Found: C, 63.11; H, 6.92; N, 13.86.

When in the above procedure, 3,4-dicarbethoxy-2-ethylfuran or 3,4-dicarbethoxy-2-propylfuran is employed as the starting material, the corresponding 2-ethyl or 2-propyl urea compound and 2-ethyl- or 5-propylfuro[3,4-d]pyrimidine-2,4-dione derivatives are obtained.

EXAMPLE 8

1-(Cyanomethyl)-4-(2,6-dimethylphenyl)piperazine

A mixture of 1-(2,6-dimethylphenyl)piperazine (23.6 g, 0.124 mol), choloracetonitrile (7.85 ml, 0.124 mol) and sodium bicarbonate (31 g, 0.372 mol) in benzene (350 ml) was heated to reflux for 16 hours, using a Dean-Stark apparatus to azeotropically remove water. The inorganic solids were removed by filtration, and the filtrate was dried over MgSO$_4$. The solvent was removed in vacuo to give the product (23.5 g, 83% yield) as a colorless solid, mp 79°–81° C. IR (KBr) 1453, 1472, 2809 and 2819 cm$^{-1}$; mass spectrum m/z 230 (MH$^+$); $^1$H NMR (CDCl$_3$) δ 2.32 (s, 6H, CH$_3$), 2.56–2.67 (m, 4H, NCH$_2$), 3.00–3.28 (m, 4H, NCH$_2$), 3.56 (s, 2H, NCCH$_2$N), 6.95 (s, 3H, Ph-H).

Theor. C$_{14}$H$_{19}$N$_3$: C, 73.33; H, 8.35; N, 18.33. Found: C, 73.10; H, 8.63; N, 18.14.

1-[1-(2-Aminoethyl)]-4-(2,6-dimethylphenyl)piperazine 1-(Cyanomethyl)-4-(2,6-dimethylphenyl)piperazine (23.3 g, 0.102 mol) was added to a suspension of LiAlH$_4$ (5.8 g, 0.152 mol) in diethyl ether over ½ hour. The mixture was heated to reflux for 5 hours. Water (6 ml) was slowly added to the mixture followed by a 15% solution of sodium hydroxide in water (6 ml) and water (20 ml). The inorganic solids were removed by filtration, and the filtrate was dried over MgSO$_4$. The solvent was removed in vacuo to give the product (16.76 g, 70% yield) as an amber oil. IR (KBr) 1475 cm$^{-1}$; mass spectrum m/z 234 (MH$^+$); $^1$H NMR (CDCl$_3$) δ 1.63 (s, 2H, NH$_2$), 2.33 (s, 6H, CH$_3$), 2.43–3.23 (m, 12H, NCH$_2$), 6.97 (s, 3H, Ph-H).

1-(3-Carboxyfuran-4-yl)-3-[4-(2,6-dimethylphenyl)piperazin-1-yl]ethylurea

4H-Furo[3,4-di][1,3]oxazine-2(1H), 4-dione (J. B. Press, et al., *J. Org. Chem.* 46, 3852 (1981)) (2.39 g, 15.6 mmol) was added to a solution of 1-[1-(2-aminoethyl)]-4-(2,6-dimethylphenyl)piperazine (4.0 g, 17.1 mmol) in tetrahydrofuran (50 ml), and the resultant mixture was stirred at room temperature for 16 hours. The white solid precipitate was collected by filtration, washed with tetrahydrofuran and air-dried to give the product (5.7 g, 95% yield) as a colorless solid, mp 136°–138° C. (dec). IR (KBr) 1540, 1567, 1628, 1683 and 3316 cm$^{-1}$; mass spectrum m/z 387 (MH$^+$); $^1$H NMR (TFA) δ 2.63 (s, 6H, Ph-CH$_3$), 3.60–4.07 (m, 4H, NCH$_2$), 4.16–4.93 (m, 8H, NCH$_2$), 7.28–7.50 (m, 3H, Ph-H), 7.88 (brs, 1H, furan-H), 8.18 (brs, 1H, furan-H).

Theor. C$_{20}$H$_{26}$N$_4$O$_4$: C, 62.16; H, 6.78; N, 14.50. Found: C, 62.09; H, 6.95; N, 14.22.

3-[2-[4-(2,6-Dimethylphenyl)piperazin-1-yl]ethyl]-furo[3,4-d]pyridimine-2,4-dione A mixture of 1-(3-carboxyfuran-4-yl)-3-[4-(2,6-dimethylphenyl)piperazin-1-yl]ethylurea (5.6 g, 14.5 mmol) and 1,1′-carbonyldiimidazole (3.05 g, 18.8 mmol) in tetrahydrofuran (100 ml) was heated to reflux for 1.5 hours. The solvent was removed in vacuo and the residue was triturated in hot water. The resultant solid was collected by filtration, washed with water and triturated in hot ethanol to give the product (0.45 g, 8% yield) as an off-white solid. The filtrate was evaporated in vacuo, and the residue was purified by flash chromatography on silica gel 60 (100 g) using 2% methanol in methylene chloride as eluant to give the product (1.47 g, 28% yield) as a colorless solid, mp 814°–186° C. (dec). IR (KBr) 1655, 1677, 1716, 2830 and 3137 cm$^{-1}$; mass spectrum m/z 369 (MH$^+$); $^1$H NMR (Me$_2$SO-d$_6$) δ 2.25 (s, 6H, Ph-CH$_3$), 2.38–2.75 (m, 6H, NCH$_2$), 2.78–3.20 (m, 4H, NCH$_2$), 4.00 (t, J=7 Hz, 2H, 3-CH$_2$), 6.83–6.98 (m, 3H, Ph-H), 7.58 (d, J=2 Hz, 1H, furan-H), 8.40 (d, J=2 Hz, 1H, furan-H) and 10.83 (brs, 1H, NH).

Theor. C$_{20}$H$_{24}$N$_4$O$_3$: C, 65.20; H, 6.57; N, 15.21. Found: C, 65.16; H, 6.65; N, 15.09.

When in the above procedure, chlorocyanoethane or chlorocyanopropane is used in place of chloroacetonitrile, the corresponding propylurea or butylurea compound and propyl]furo[3,4-d]pyrimidine-2,4-dione or butyl]furo[3,4-d]pyrimidine-2,4-dione derivative are obtained.

EXAMPLE 9

1-Acetyl-3-[2-[4-(2-methoxyphenyl)piperazin-1-yl]ethyl]furo[3,4-d]pyrimidine-2,4-dione A solution of 3-[2-[4-(2-methoxyphenyl)piperazin-1-yl]ethyl]furo[3,4-d]pyrimidine-2,4-dione (3.0 g, 8.10 mmol) in acetic anhydride (50 ml) was heated to reflux for 16 hours. The solvent was removed in vacuo. The oily residue was dissolved in toluene, and the solvent was removed in vacuo, and the process was repeated. The brown oil crystallized from diethyl ether to give the product (2.77 g, 83% yield) as an off-white solid, mp 128°–131° C. IR (KBr) 2820, 1742, 1717, 1702 and 1621 cm$^{-1}$; mass spectrum m/z 413 (MH$^+$); $^1$H NMR (CDCl$_3$) δ 2.50–2.87 (m, 6H, NCH$_2$), 2.72 (s, 3H, COCH$_3$), 2.92–3.18 (m, 4H, NCH$_2$), 3.82 (s, 3H, OCH$_3$), 4.18 (t, J=7 Hz, 2H, 3-CH$_2$), 6.67–7.02 (m, 4H, Ph-H), 8.08 (d, J=2 Hz, 1H, furan-H), 8.21 (d, J=2 Hz, 1H, furan-H).

Theor. C$_{21}$H$_{24}$N$_4$O$_5$: C, 61.16; H, 5.87; N, 13.58. Found: C, 62.38; H, 5.95; N, 13.46.

EXAMPLE 10

1-Butyl-3-[2-[4-(2-methoxyphenyl)piperazin-1-yl]ethyl]furo[3,4-d]pyrimidine-2,4-dione 3-[2-[4-(2-Methoxyphenyl)piperazin-1-yl]ethyl]furo[3,4-d]pyrimidine-2,4-dione (1.8 g, 4.85 mmol) was added to a suspension of sodium hydride (60% in mineral oil, 0.28 g, 7.1 mmol, prewashed with pentane) in N,N-dimethylformamide (50 ml), and the mixture was stirred at room temperature for 1 hour. Iodobutane (0.8 ml, 7.0 mmol) was added to the resultant solution, and the mixture was stirred at room temperature for 16 hours. The mixture was poured into ice water (200 ml), and the resultant solid was collected by filtration, washed with water, and recrystallized from ethanol to give the product (1.22 g, 59% yield) as a colorless solid, mp 112°–114° C. IR (KBr) 1502, 1648, 1670, 1716, 2822 and 2937 cm$^{-1}$; mass spectrum m/z 427 (MH+); $^1$H NMR (CDCl$_3$) δ 0.97 (t, J=8 Hz, 3H, CH$_2$CH$_3$), 1.14–2.00 (m, 4H, CH$_2$CH$_2$CH$_3$), 2.53–2.89 (m, 6H, NCH$_2$), 2.92–3.20 (m, 4H, NCH$_2$), 3.78 (t, J=8 Hz, 2H, 1-CH$_2$), 3.85 (s, 3H, OCH$_3$), 4.19 (t, J=7 Hz, 2H, 3-CH$_2$), 6.77–7.10 (m, 4H, Ph-H), 7.33 (d, J=2 Hz, 1H, furan-H), 8.06 (d, J=2 Hz, 1H, furan-H).

Theor. C$_{23}$H$_{30}$N$_4$O$_4$: C, 64.77; H, 7.09; N, 13.14. Found: C, 64.48; H, 7.30; N, 12.85.

When in the above procedure, ethyl iodide, decyl iodide, 1-bromo-2-methylpropane or 1-bromo-2-ethylbutane is employed as the alkylating agent, the corresponding 1-ethyl, 1-decyl, 1-(2-methylpropyl) or 1-(2-ethylbutyl) derivative is obtained.

When in the above procedure, allyl bromide, 4-bromo-1-butene, 6-bromo-1-hexene or propargyl bromide is used as the alkylating agent, the corresponding 1-(propen-3-yl), 1-(buten-4-yl), 1-(hexen-6-yl) or 1-(propyn-3-yl) derivative is obtained.

EXAMPLE 11

1-Methyl-3-[2-[4-(2-methoxyphenyl)piperazin-1-yl]ethyl]furo[3,4-d]pyrimidine-2,4-dione 3-[2-[4-(2-Methoxyphenyl)piperazin-1-yl]ethyl]furo[3,4-d]pyrimidine-2,4-dione (2.03 g, 5.48 mmol) was added to a suspension of sodium hydride (60% in mineral oil, 0.24 g, 6.03 mmol, prewashed with pentane) in N,N-dimethylformamide (50 ml), and the mixture was stirred at room temperature for 1 hour. Iodomethane (0.42 ml, 6.75 mmol) was added to the resultant solution, and the mixture was stirred at room temperature for 2.5 days. The mixture was poured into ice water (200 ml), and the resultant solid was collected by filtration, washed with water, and air-dried. The solid was dissolved in 2% methanol in methylene chloride and eluted through a pad of magnesium silicate. The eluate was concentrated in vacuo, and the resultant solid was triturated in diethyl ether to give the product (0.775 g, 37% yield) as a colorless solid, mp 150°–152° C. IR (KBr) 1501, 1648, 1673 and 1712 cm$^{-1}$; mass spectrum m/z 385 (MH+); $^1$H NMR (CDCl$_3$) δ 2.53–2.91 (m, 6H, NCH$_2$), 2.95–3.22 (m, 4H, NCH$_2$), 3.33 (s, 3H, NCH$_3$), 3.83 (s, 3H, OCH$_3$), 4.18 (t, J=7 Hz, 2H, 3-CH$_2$), 6.73–7.00 (m, 4H, Ph-H), 7.28 (d, J=2 Hz, 1H, furan-H), 8.02 (d, J=2 Hz, 1H, furan-H).

Theor. C$_{20}$H$_{24}$N$_4$O$_4$: C, 62.49; H, 6.29; N, 14.57. Found: C, 62.44; H, 6.39; N, 14.70.

EXAMPLE 12

3-[2-[4-(2-Methoxyphenyl)piperazin-1-yl]ethyl]-1-(2,2-dimethyl-1-oxopropyl)furo[3,4-d]pyrimidine-2,4-dione Trimethylacetylchloride (0.91 ml, 7.42 mmol) was added to a solution of 3-[2-[4-(2-methoxyphenyl)piperazin-1-yl]ethyl]furo[3,4-d]pyrimidine-2,4-dione (2.5 g, 6.74 mmol) and triethylamine (2.8 ml, 20.2 mmol) in methylene chloride (100 ml), and the resultant mixture was stirred at room temperature for 16 hours. The mixture was washed with saturated aqueous sodium bicarbonate and dried over magnesium sulfate. The product was purified by flash chromatography on silica gel 60 (200 g) using 1% methanol in methylene chloride as eluant to give the product (1.36 g, 44% yield) as a colorless solid, mp 86°–88° C. IR (KBr) 1735, 1697 and 1623 cm$^{-1}$; mass spectrum m/z 455 (MH+); $^1$H NMR (CDCl$_3$) δ 1.42 (s, 9H, CCH$_3$), 2.55–2.83 (m, 6H, NCH$_2$), 2.93–3.17 (m, 4H, NCH$_2$), 3.83 (s, 3H, OCH$_3$), 4.15 (t, J=7 Hz, 2H, 3-CH$_2$), 6.80–6.93 (m, 4H, Ph-H), 7.18 (d, J=2 Hz, 1H, furan-H), 8.03 (d, J=2 Hz, 1H, furan-H).

Theor. C$_{24}$H$_{30}$N$_4$O$_5$: C, 63.42; H, 6.65; N, 12.33. Found: C, 63.73; H, 6.81; N, 12.01.

When in the above procedure, hexanoyl chloride or isobutyryl chloride are employed as the acylating agent, the corresponding 1-oxohexyl or 1-(2-methyl-1-oxopropyl) derivative is obtained.

EXAMPLE 13

Ethyl 3-[2-[4-(2-methoxyphenyl)piperazin-1-yl]ethyl]furo[3,4-d]pyrimidine-2,4-dione-1-butanoate 3-[2-[4-(2-Methoxyphenyl)piperazin-1-yl]ethyl]furo[3,4-d]pyrimidine-2,4-dione (1.8 g, 4.85 mmol) was added to a suspension of sodium hydride (60% in mineral oil, 0.29 g, 7.25 mmol, prewashed with pentane) in N,N-dimethylformamide (50 ml), and the mixture was stirred at room temperature for 1 hour. Ethyl 4-bromobutanoate (0.9 ml, 6.29 mmol) was added to the resultant solution, and the mixture was stirred at room temperature for 16 hours. The mixture was poured into ice water (200 ml) and extracted with methylene chloride (100 ml), washed with cold 1N sodium hydroxide solution (2×50 ml), washed with water (2×50 ml) and dried over magnesium sulfate. The solvent was removed in vacuo. The resultant oil was purified by flash chromatography on silica gel 60 (100 g) using 1% methanol in methylene chloride as eluant to give the product (0.470 g, 20% yield) as an off-white solid, mp 88°–90° C. IR (KBr) 1640, 1671 and 1720 cm$^{-1}$; mass spectrum m/z 485 (MH+); $^1$H NMR (CDCl$_3$) δ 1.25 (t, J=7 Hz, 3H, CH$_2$CH$_3$), 1.67–3.20 (m, 14H, NCH$_2$, CH$_2$CH$_2$CO$_2$), 3.70–4.37 (m, 6H, 1-CH$_2$, 3-CH$_2$, CO$_2$CH$_2$), 3.83 (s, 3H, OCH$_3$), 6.67–7.00 (m, 4H, Ph-H), 7.45 (d, J=2 Hz, 1H, furan-H), 8.03 (d, J=2 Hz, 1H, furan-H).

Theor. C$_{25}$H$_{32}$N$_4$O$_6$: C, 61.97; H, 6.66; N, 11.56. Found: C, 62.27; H, 6.97; N, 11.31.

When in the above procedure, methyl 3-bromopropionate or ethyl 5-bromovalerate is employed as the alkylating agent, the corresponding 1-[2-(methoxycarbonyl)ethyl] or 1-[4-(ethoxycarbonyl)butyl] derivative is obtained.

EXAMPLE 14

1-Benzoyl-3-[2-[4-(2-methoxyphenyl)piperazin-1-yl]ethyl]furo[3,4-d]pyrimidine-2,4-dione 3-[2-[4-(2-Methoxyphenyl)piperazin-1-yl]ethyl]-furo[3,4-d]pyrimidine-2,4-dione (2.5 g, 6.74 mmol) was added to a suspension of sodium hydride (60% in mineral oil. 0.32 g, 8.1 mmol, prewashed with pentane) in N,N-dimethylformamide (40 ml), and the mixture was stirred at room temperature for 1.5 hours, Benzoyl chloride (0.86 ml, 7.41 mmol) was added to the resultant solution, and the mixture was stirred at room temperature for 16 hours. The mixture was concentrated in vacuo and treated with water (50 ml). The resultant solid was collected by filtration, washed with water, and air-dried. The product was purified by flash chromatography on silica gel 60 (90 g) using 2% methanol in methylene chloride as eluant to give the product (1.63 g, 51% yield) as a colorless solid, mp 147°-148° C. IR (KBr) 1500, 1625, 1697 and 1739 cm$^{-1}$; mass spectrum m/z 375 (MH+); $^1$H NMR (CDCl$_3$) δ 2.58-2.87 (m, 4H, NCH$_2$), 2.96-3.20 (m, 4H, NCH$_2$), 3.86 (s, 3H, OCH$_3$), 4.15 (t, J=7 Hz, 2H, 3-CH$_2$), 6.80-7.00 (m, 4H, Ph-H), 7.33-7.83 (m, 5H, Ph-H), 8.05 (d, J=2 Hz, 1H, furan-H), 8.15 (d, J=2 Hz, 1H, furan-H).

Theor. C$_{26}$H$_{26}$N$_4$O$_5$: C, 65.81; H, 5.52; N, 11.80. Found: C, 65.65; H, 5.38; N, 11.70.

When in the above procedure, 4-chlorobenzoyl chloride or 4-methoxybenzoyl chloride is employed as the alkylating agent, the corresponding 1-(4-chlorobenzoyl) or 1-(4-methoxybenzoyl) derivative is obtained.

EXAMPLE 15

Ethyl 3-[2-[4-(2-methoxyphenyl)piperazin-1-yl]ethyl]-2,4-dioxofuro[3,4-d]pyrimidine-1-carboxylate 3-[2-[4-(2-Methoxyphenyl)piperazin-1-yl]ethyl]-furo[3,4-d]pyrimidine-2,4-dione (2.0 g, 5.40 mmol) was added to a suspension of sodium hydride (60% in mineral oil, 0.26 g, 6.47 mmol, prewashed with pentane) in N,N-dimethylformamide (50 ml), and the mixture was stirred at room temperature for 1 hour. Ethyl chloroformate (0.62 ml, 6.47 mmol) was added to the resultant solution, and the mixture was stirred at room temperature for 16 hours. The mixture was poured into ice water (300 ml), and the resultant solid was collected by filtration, washed with water, and air-dried. The solid was recrystallized from methylene chloride/hexane to give the product (1.61 g, 67% yield) as an off-white solid, mp 105°-106° C. IR (KBr) 1499, 1625, 1702 and 1747 cm$^{-1}$; mass spectrum m/z 443 (MH+); $^1$H NMR (CDCl$_3$) δ 1.45 (t, J=7 Hz, 3H, CH$_2$CH$_3$), 2.52-2.88 (m, 6H, NCH$_2$), 2.93-3.18 (m, 4H, NCH$_2$), 3.83 (s, 3H, OCH$_3$), 4.18 (t, J=7 Hz, 2H, 3-CH$_2$), 4.50 (q, J=7 Hz, 2H, OCH$_2$CH$_3$), 6.78-7.02 (m, 4H, Ph-H), 7.87 (d, J=2 Hz, 1H, furan-H), 8.05 (d, J=2 Hz, 1H, furan-H).

Theor. C$_{22}$H$_{26}$N$_4$O$_6$: C, 59.72; H, 5.92; N, 12.66. Found: C, 59.56; H, 5.88; N, 12.52.

EXAMPLE 16

1-Methyl-3-[2-(4-phenylpiperazin-1-yl)ethyl]furo[3,4-d]pyrimidine-2,4-dione

3-[2-(4-Phenylpiperazin-1-yl)ethyl]furo[3,4-d]pyrimidine-2,4-dione (2.7 g, 7.93 mmol) was added to a suspension of sodium hydride (60% in mineral oil, 0.38 g, 9.5 mmol, prewashed with pentane) in N,N-dimethylformamide (40 ml), and the mixture was stirred at room temperature for 1.5 hours. Iodomethane (0.54 ml, 8.7 mmol) was added to the resultant solution, and the mixture was stirred at room temperature for 16 hours. The mixture was concentrated in vacuo, treated with water (50 ml) and extracted with methylene chloride (2×50 ml). The methylene chloride solutions were combined, washed with 1N sodium hydroxide solution (100 ml), washed with water (100 ml), and dried over magnesium sulfate. The product was purified by flash chromatography on silica gel 60 (90 g) using 2% methanol in methylene chloride as eluant to give the product (1.76 g, 63% yield) as a colorless solid, mp 144°-145° C. IR (KBr) 1505, 1650, 1667 and 1709 cm$^{-1}$; mass spectrum m/z 355 (MH+); $^1$H NMR (CDCl$_3$) δ 2.53-2.88 (m, 6H, NCH$_2$), 3.07-3.32 (m, 4H, NCH$_2$), 3.35 (s, 3H, NCH$_3$), 4.18 (t, J=7 Hz, 2H, 3-CH$_2$), 6.67-7.41 (m, 6H, Ph-H, furan-H), 8.02 (d, J=2 Hz, 1H, furan-H).

Theor. C$_{19}$H$_{22}$N$_4$O$_3$: C, 64.39; H, 6.26; N, 15.81. Found: C, 63.92; H, 6.35; N, 15.62.

EXAMPLE 17

1-(Cyanomethyl)-4-(2-fluorophenyl)piperazine

A mixture of 1-(2-fluorophenyl)piperazine (10.0 g, 55.5 mmol), chloroacetonitrile (3.51 ml, 55.5 mmol) and sodium bicarbonate (14 g, 0.166 mol) in benzene (200 ml) was heated to reflux for 16 hours, using a Dean-Stark apparatus to azeotropically remove water. The inorganic solids were removed by filtration, and the filtrate was dried over magnesium sulfate. The solvent was removed in vacuo to give an oil which crystallized from hexane to give the product (9.2 g, 76% yield) as a colorless solid, mp 70°-72° C. IR (KBr) 1460, 1478, 1649, 1655, 1673 and 1706 cm$^{-1}$; mass spectrum m/z 220 (MH+); $^1$H NMR (CDCl$_3$) δ 2.63-2.88 (m, 4H, NCH$_2$), 3.03-3.26 (m, 4H, NCH$_2$), 3.53 (s, 2H, NCCH$_2$N), 6.83-7.07 (m, 4H, Ph-H).

1-[1-(2-Aminoethyl)-4-(2-fluorophenyl)piperazine 1-(Cyanomethyl)-4-(2-fluorophenyl)piperazine (9.0 g, 41.0 mmol) was added in portions to a suspension of LiAlH$_4$ (2.34 g, 61.6 mmol) in diethyl ether (200 ml) over ½ hour. The mixture was heated to reflux for 5 hours. Water (3 ml) was slowly added to the mixture, followed by a 15% solution of sodium hydroxide in water (3 ml) and water (9 ml). The inorganic solids were removed by filtration, and the filtrate was dried over MgSO$_4$. The solvent was removed in vacuo to give the product (16.76 g, 70% yield) as an amber oil which slowly crystallized to a colorless solid, mp 108°-112° C. IR (KBr) 1502 cm$^{-1}$; mass spectrum m/z 224 (MH+); $^1$H NMR (CDCl$_3$) δ1.38 (s, 2H, NH$_2$), 2.33-3.23 (m, 12H, NCH$_2$), 6.80-7.06 (m, 4H, Ph-H).

1-(3-Carboxyfuran-4-yl)-3-[4-(2-fluorophenyl)piperazin-1-yl]ethylurea

4H-Furo[3,4-d][1,3]oxazine-2(1H), 4-dione (Press, J. B. et al., *J. Org. Chem.* 46 3853 (1981)) (2.0 g, 13.1 mmol) was added to a solution of 1-[1-(2-aminoethyl)]-4-[2-fluorophenyl)piperazine (3.2 g, 14.4 mmol) in tetrahydrofuran (70 ml), and the resultant mixture was stirred at room temperature for 4 hours. The white solid precipitate was collected by filtration, washed with tetrahydrofuran and air-dried to give the product (4.3 g, 79% yield) as a colorless solid, mp 208°-210° C. (dec). IR (KBr) 1540, 1567, 1628, 1683 and 3316 cm$^{-1}$; mass spectrum m/z 377 (MH+); $^1$H NMR (Me$_2$SO-d$_6$) δ 2.40-3.47 (m, 12H, NCH$_2$), 6.76-7.27 (m, 4H, Ph-H), 7.87 (d, J=2 Hz, 1H, furan-$\underline{H}$), 7.98 (d, J=2 Hz, 1H, furan-$\underline{H}$).

Theor. $C_{18}H_{21}FN_4O_4$: C, 57.44; H, 5.62; N, 14.89. Found: C, 57.38; H, 5.97; N, 14.74.

3-[2-[4-(2-Fluorophenyl)piperazin-1-yl]ethyl]furo[3,4-d]pyrimidine-2,4-dione

A mixture of 1-(3-carboxyfuran-4-yl)-3-[4-(2-fluorophenyl)piperazin-1-yl]ethylurea (4.1 g, 10.9 mmol) and 1,1'-carbonyldiimidazole (2.30 g, 14.2 mmol) in tetrahydrofuran (100 ml) was heated to reflux for 2 hours. The solvent was removed in vacuo, and the residue was triturated in hot water. The resultant solid was collected by filtration, washed with water, and triturated in hot ethanol to give the product (3.2 g, 82% yield) as a pale pink solid, mp 208°–209° C. (dec). IR (KBr) 1650, 1673 and 1707 cm$^{-1}$; mass spectrum m/z 359 (MH+); $^1$H NMR (Me$_2$SO-d$_6$) δ 2.33–2.76 (m, 6H, NCH$_2$), 2.83–3.13 (m, 4H, NCH$_2$), 3.96 (t, J=7 Hz, 2H, 3-C$\overline{H}_2$), 6.76–7.27 (m, 4H, Ph-$\overline{H}$), 7.60 (d, J=2 Hz, 1H, furan-$\overline{H}$), 8.42 (d, J=2 Hz, 1H, furan-$\underline{H}$) and 10.90 (bs, 1H, N$\underline{H}$).

Theor. $C_{18}H_{19}FN_4O_3$: C, 60.33; H, 5.34; N, 15.63; F, 5.30. Found: C, 60.27; H, 5.57; N, 15.56; F, 5.26.

EXAMPLE 18

Vasodilatory Activity

The vasodilatory activity of the above compounds was tested as follows. Adult mongrel dogs were anesthetized and surgically prepared for electromagnetic measurement of renal artery blood flow. A carotid artery was cannulated for measuring arterial blood pressure and drugs were administered intravenously or intraarterially (renal artery). Heart rate was monitored by a cardiotachometer. Renal vascular resistance (RVR) was calculated as the ratio of mean arterial blood pressure/renal artery blood flow. Dopamine was infused intravenously at 3 μg/kg/min for 10 minutes (1 ml/min) to determine responsiveness of each dog to renal dopmaine receptor stimulation. Cumulative dose-response data were obtained by infusing the test drug at progressively increasing (usually three-fold) infusion rates, each dose being infused for five minutes. The maximum percent increase from pre-drug control in renal artery blood flow (RBF) or decrease in renal vascular resistance (RVR) was quantitated for each infusion dose. The results for representative compounds are shown in Table I.

TABLE I

| Vasodilatory Effects of Representative Furo-pyrimidine-2,4-dione Derivatives in Anesthetized Dog | | | |
|---|---|---|---|
| Compound (Example) | Total Cumulative Dose (mg/kg i.v.) | Percent Change From Pre-Drug Baseline | |
| | | RBF | RVR |
| 1 | 1.2 | +5 | −28 |
| 3 | 6.2 | +23 | −38 |
| 8 | 6.2 | +5 | −18 |
| 12 | 1.2 | +40 | −47 |

EXAMPLE 19

Antihypertensive Activity

The antihypertensive activity of the compounds was tested as follows. Adult male spontaneously hypertensive rats (SHR) were placed in restrainers in a chamber warmed to 32° C. A standard indirect method employing a pneumatic pulse transducer and inflatable tail cuff was used to measure systolic blood pressure (SBP) in the conscious state. After baseline SBPs were recorded, groups of 4–6 SHR received a single oral dose of drug or vertical (0.5% methylcellulose) administered with a gavage tube at doses of 0.5–20 mg/kg. SBPs were obtained at ½, 1, 2, 3 and 4 hours post-treatment. Changes in SBPs were statistically compared to the vehicle effect using Students t test at p=0.05. The results for representative compounds are shown in Table II.

TABLE II

| Antihypertensive Effect of Representative Furopyrimidine-2,4-dione Derivatives | | |
|---|---|---|
| Compound (Example) | Dose (mg/kg) | Change from Pre-Drug Systolic Blood Pressure (mmHg) |
| 1 | 5.0 | −86 |
| 2 | 5.0 | −43 |
| 3 | 2.5 | −56 |
| 6 | 5.0 | −37 |
| 9 | 5.0 | −86 |
| 11 | 5.0 | −62 |

What is claimed is:

1. A compound of the formula

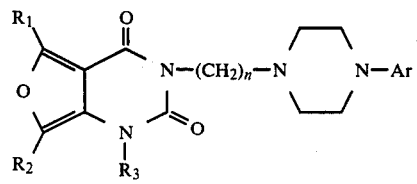

where $R_1$ and $R_2$ are the same or different and are hydrogen or $C_1$–$C_3$ alkyl;

$R_3$ is hydrogen, $C_1$–$C_{10}$ alkyl, $C_3$–$C_8$ branched-chain alkyl, $C_3$–$C_8$ alkenyl, $C_3$–$C_6$ alkynyl, —(CH$_2$)$_m$—CO$_2$R$_4$ or —COR$_5$;

$R_4$ is hydrogen, $C_1$–$C_3$ alkyl, pharmaceutically acceptable alkali metal ion, pharmaceutically acceptable alkaline earth metal ion or a pharmaceutically acceptable quaternary ammonium species;

$R_5$ is $C_1$–$C_{10}$ alkyl, $C_3$–$C_{10}$ branched-chain alkyl, $C_1$–$C_3$ alkoxy or Ar;

Ar is

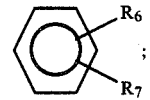

$R_6$ and $R_7$ are the same or different and are hydrogen, F, Cl, Br, NO$_2$, CF$_3$, $C_1$–$C_3$ alkyl, acetyl, $C_1$–$C_3$ alkoxy or acetamido;

m is 2–6; and n is 2–4.

2. A compound of claim 1 selected from the group consisting of 3-[2-[4-(2-methoxyphenyl)piperazin-1-yl]ethyl]furo[3,4-d]pyrimidine-2,4-dione; 3-[2-[4-(2-methylphenyl)piperazin-1-yl]ethyl]furo[3,4-d]pyrimidine-2,4-dione; 3-[2-(4-phenylpiperazin-1-yl)ethyl]furo[3,4-d]pyrimidine-2,4-dione; 3-[2-[4-(2-chlorophenyl)piperazin-1-yl]ethyl]furo[3,4-d]pyrimidine-2,4-dione; 3-[2-[4-(3-methoxyphenyl)piperazin-1-yl]ethyl]furo[3,4-d]pyrimidine-2,4-dione; 3-[2-[4-(4-methoxyphenyl)piperazin-1-yl]ethyl]furo[3,4-d]pyrimidine-2,4-dione; 3-[2-[4-(2,6-dimethylphenyl)piperazin-1-yl]e- thyl]furo[3,4-d]pyrimidine-2,4-dione; and 3-[2-[4-(2-fluorophenyl)piperazin-1-yl]ethyl]furo[3,4-d]pyrimidine-2,4-dione.

3. A compound of claim 1 which is 5,7-dimethyl-3-[2-[4-(2-methoxyphenyl)piperazin-1-yl]ethyl]furo[3,4-d]pyrimidine-2,4-dione.

4. A compound of claim 1 selected from the group consisting of 1-acetyl-3-[2-[4-(2-methoxyphenyl)piperazin-1-yl]ethyl]furo[3,4-d]pyrimidine-2,4-dione; 3-[2-[4-(2-methoxyphenyl)piperazin-1-yl]ethyl]-1-(2,2-dimethyl-1-oxopropyl)furo[3,4-d]pyrimidine-2,4-dione; 1-benzoyl-3-[2-[4-(2-methoxyphenyl)piperazin-1-yl]ethyl]furo[3,4-d]pyrimidine-2,4-dione; and ethyl 3-[2-[4-(2-methoxyphenyl)piperazin-1-yl]ethyl]-2,4-dioxofuro-[3,4-d]pyrimidine-1-carboxylate.

5. A compound of claim 1 selected from the group consisting of 1-butyl-3-[2-[4-(2-methoxyphenyl)piperazin-1-yl]ethyl]furo[3,4-d]pyrimidine-2,4-dione; 1-methyl-3-[2-[4-(2-methoxyphenyl)piperazin-1-yl]ethyl]-furo[3,4-d]pyrimidine-2,4-dione; and 1-methyl-3-[2-(4-phenylpiperazin-1-yl)ethyl]furo[3,4-d]pyrimidine-2,4-dione.

6. A compound of claim 1 which is ethyl 3-[2-[4-(2-methoxyphenyl)piperazin-1-yl]ethyl]furo[3,4-d]pyrimidine-2,4-dione-1-butanoate.

* * * * *